(12) United States Patent
Wolpa

(10) Patent No.: US 7,959,588 B1
(45) Date of Patent: Jun. 14, 2011

(54) PRESSUREABLE COMPRESSION WRAP

(76) Inventor: Mark Wolpa, Berkeley, CA (US)

( * ) Notice: Subject to any disclaimer, the term of this patent is extended or adjusted under 35 U.S.C. 154(b) by 49 days.

(21) Appl. No.: 11/740,219

(22) Filed: Apr. 25, 2007

(51) Int. Cl.
*A61F 5/00* (2006.01)
*A61F 13/00* (2006.01)
*A61F 7/00* (2006.01)

(52) U.S. Cl. ............... 602/13; 602/2; 602/14; 602/60; 602/61; 607/108; 607/111; 607/112

(58) Field of Classification Search .......... 602/2, 13, 602/14, 30, 60–62; 607/96, 108–112, 5, 607/13, 2
See application file for complete search history.

(56) References Cited

U.S. PATENT DOCUMENTS

| | | | | |
|---|---|---|---|---|
| 1,175,718 A | * | 3/1916 | Crowe | 602/30 |
| 1,665,030 A | * | 4/1928 | Hartwig | 602/30 |
| 2,589,791 A | * | 3/1952 | Fine | 602/30 |
| 3,063,446 A | * | 11/1962 | Levitt | 602/30 |
| 3,476,102 A | * | 11/1969 | Sarnoff | 126/204 |
| 4,644,940 A | * | 2/1987 | Nakamura | 602/30 |
| 5,062,414 A | * | 11/1991 | Grim | 602/19 |
| 5,354,260 A | * | 10/1994 | Cook | 602/13 |
| 5,453,083 A | * | 9/1995 | Kasahara | 602/30 |
| 5,496,358 A | * | 3/1996 | Rosenwald | 607/108 |
| 5,928,173 A | * | 7/1999 | Unruh | 602/30 |
| 6,001,119 A | * | 12/1999 | Hampson et al. | 606/202 |
| 6,093,163 A | * | 7/2000 | Chong et al. | 602/30 |
| 2002/0193717 A1 | * | 12/2002 | Burns et al. | 602/6 |
| 2006/0155233 A1 | * | 7/2006 | Huber et al. | 602/30 |

* cited by examiner

*Primary Examiner* — Kim M Lewis
(74) *Attorney, Agent, or Firm* — Michael I. Kroll

(57) ABSTRACT

A compression wrap for application to body members having a top layer and a bottom layer with an inflatable bladder of smaller dimension positioned therebetween, an interiorly positioned pocket for insertion of a gel pack and a hand-bulb for increasing the pressure within the bladder and thereby applying pressure to the gel pack. To remove the compression wrap, the hand bulb is mounted in a reverse direction and pumped to deflate the bladder.

4 Claims, 11 Drawing Sheets

PRESSUREABLE COMPRESSION WRAP

BACKGROUND OF THE INVENTION

1. Field of the Invention

The present invention relates generally to compression wraps and, more specifically, to a compression wrap for application to body members having a top layer and a bottom layer with an inflatable bladder of smaller dimension positioned therebetween, an interiorly positioned pocket for insertion of a gel pack and a hand-bulb for increasing the pressure within the bladder and thereby applying pressure to the gel pack. A release valve is incorporated into the bulb for selectively releasing the bladder pressure.

2. Description of the Prior Art

There are other compression wraps designed for appendage application. Typical of these is U.S. Pat. No. 1,567,931 issued to Epler on Dec. 29, 1925.

Another patent was issued to Poux on Jul. 24, 1951 as U.S. Pat. No. 2,562,121. Yet another U.S. Pat. No. 3,882,867 was issued to Moran on May 13, 1975 and still yet another was issued on May 27, 1980 to Henderson as U.S. Pat. No. 4,204,543.

Another patent was issued to Gordon, et al. on Jun. 2, 1987 as U.S. Pat. No. 4,669,476. Yet another U.S. Pat. No. 5,423,875 was issued to Kehe on Jun. 13, 1995. Another was issued to Rosenwald on Mar. 5, 1996 as U.S. Pat. No. 5,496,358 and still yet another was issued on Jun. 16, 1998 to Kostopoulos as U.S. Pat. No. 5,766,235.

Another patent was issued to 1,467,729 on Mar. 23, 1977 as U.K. Patent No. GB 1467729. Yet another International Patent Application No. WO 95/03016 was issued to Hadtke on Feb. 2, 1995. Another was issued to Kolan, et al. on Dec. 12, 1995 as Ireland Patent No. IR950163 and still yet another was issued on Jan. 27, 2005 to Parish as International Patent Application No. WO 2005/007060.

U.S. Pat. No. 1,567,931

Inventor

Percy H. Epler

Issued

Dec. 29, 1925

A compress comprising a plurality of layers of absorbent material on one side and a rubber lining on the other side and having a longitudinal seam along the bottom and two seams extending upwardly from the ends thereof to unite the several layers of materials along said seams and form a pocket, said pocket being open at the top so as to be capable of receiving ice or water therein.

U.S. Pat. No. 2,562,121

Inventor

Noel J. Poux

Issued

Jul. 24, 1951

An article comprising an elongated body member made of relatively thin and flexible material, at least one permanently sealed air-containing compartment arranged on one side of said body member, a plurality of permanently sealed and independent liquid-containing compartments arranged on the opposite side of said body member so as to be disposed in superimposed relation to said first-mentioned compartment.

U.S. Pat. No. 3,882,867

Inventor

Harold J. Moran

Issued

May 13, 1975

A wrap for use as a cold compress, preferably on the legs of horses, is disclosed. The wrap preferably includes a layer of highly compressed absorbent material, such as artificial sponge, a resilient net-like supportive backing sewn thereto and having a tongue extending from one end thereof, and adjustable fastening means whereby the wrap may be held in place on the leg. If compressed sponge material is used, it expands greatly upon being doused with water producing a firm fit. The fine net-like supportive backing promotes rapid evaporation by allowing maximum exposure of the water to the atmosphere, thus cooling the horse's leg.

U.S. Pat. No. 4,204,543

Inventor

Mary H. Henderson

Issued

May 27, 1980

A band of textile material is disclosed containing a pocket with an opening for receiving and storing a bag of freezable liquid or semi-liquid material. The band has an elastic or adjustable means associated with it for maintaining the pocket and the bag contained therein in direct contractive engagement with the part of the anatomy to be cooled.

U.S. Pat. No. 4,669,476

Inventor

Tim H. Gordon

Issued

Jun. 2, 1987

A bandage for the simultaneous application of cold therapy and compression comprises an elastic material for wrapping around a portion of a user's body. A refrigeratable pack includes a tab extending therefrom. The refrigeratable pack is removably held on said elastic material during use so that the tab is accessible for grasping by the user.

U.S. Pat. No. 5,423,875

Inventor

David Kehe

Issued

Jun. 13, 1995

The universal moist ice wrap is made of two parts, a sleeve designed to allow the crushing and containment of real ice, and an elastic strap called a compression strap which can be used to fasten the sleeve in place and increase cold transmission at the desire of the user. The sleeve is made of two faces, one of water-permeable material and the other of a water-impermeable material, sealed with a watertight edge and one edge opened, which can be closed at will using the Velcro® edging fastened to the opposing materials. Straps and sleeves may be joined in a series of different combinations to allow the sleeve to be used by humans and animals for cryotherapy at the lowest possible safe temperature which can be applied against the skin.

U.S. Pat. No. 5,496,358

Inventor

Mark A. Rosenwald

Issued

Mar. 5, 1996

A thermal wrap is disclosed for application to body members, especially joints and limbs. It comprises a pouch for containing a thermal medium and which is constructed of a flexible elastic cloth. The pouch is mounted on a support member, also constructed of a flexible elastic cloth, which is adapted to wrap around a limb or joint. The support member is provided with a wrap fastener such as a hook and loop fastener which is adjustable to establish the desired degree of compression on the affected area. The wrap as applied to a knee and wrist is provided with cinch bands which encircle the limb at locations above and below the pouch. This arrangement provides compression under the bandwidth of the pouch which is independently adjustable relative to the compression under the cinch bands. Additionally, a pressurized air bladder may be provided to independently adjust the compression under the bandwidth of the pouch. Other advantageous features of the wrap that specifically relate to thermal wrapping an ankle and shoulder are also disclosed.

U.S. Pat. No. 5,766,235

Inventor

Thomas J. Kostopoulos

Issued

Jun. 16, 1998

Thick opaque ceramic coatings are used to protect delicate microelectronic devices against excited energy sources, radiation, light, abrasion, and wet etching techniques. The thick opaque ceramic coating are prepared from a mixture containing phosphoric anhydride, i.e., phosphorous pentoxide ($P_2O_5$), and a pre-ceramic silicon-containing material. It is preferred to also include tungsten carbide (WC) and tungsten metal (W) in the coating mixture. The coating is pyrolyzed to form a ceramic $SiO_2$ containing coating. A second coating of plasma enhanced chemical vapor deposited (PECVD) silicon carbide (SiC), diamond, or silicon nitride ($Si_3N_4$), can be applied over the thick opaque ceramic coating to provide hermeticity. These coatings are useful on patterned wafers, electronic devices, and electronic substrates. The thick opaque ceramic coating is unique because it is resistant to etching using wet chemicals, i.e., acids such as $H_3PO_4$ and $H_2SO_4$, or bases.

U.K. Patent Number GB 1467729

Inventor

Cryo-Med Devices, Inc

Issued

Mar. 23, 1977

An inflatable wrap-around compress 41 comprises three layers of flexible plastics material 60, 61 and 62, layers 60 and 62 being joined together by a heat seal 63 to form an enclosed interior chamber, layer 61 lies between layers 60 and 62 and is joined to layer 62 by heat seals 65 forming a winding channel 66 in between layers 61 and 62 over substantially the whole surface of layer 61 with one end 67 of channel 66 communicating with the interior chamber and the other end being connected with an inlet fitting 43, and an outlet fitting 44 having a pressure-relief valve 46 communicating through layer 60 between the interior chamber and the ambient atmosphere, whereby in use the compress is secured around a limb by locking strips 45, and compressed refrigerant supplied to inlet fitting 43 volatilizes in channel 66 thereby cooling the compress, and gasified refrigerant exhausting into the chamber inflates the compress to apply pressure to the patient, the pressure being determined by valve 46. A quick release valve 48 is provided so that the compress may be rapidly deflated. A tank of liquefied refrigerant may be provided, connected to the inlet of the compress by a tube, and a flow control and a check-valve provided to control the flow of refrigerant. In an alternative embodiment, FIG. 8 (not shown), the channel is in the form of a spiral. Other embodiments are an inflatable sleeve for treating a horse's leg; an inflatable mitten; and an inflatable boot. The compresses may be constructed so that the channel is in a wall portion either adjacent to, or distant from the area to be treated.

International Patent Application Number WO 95/03016

Inventor

Frederick B. Hadtke

Issued

Feb. 2, 1995

An apparatus (10) for treating injuries includes a first layer (42) of flexible material (12) and a second layer (34) of flexible material (12) coupled to the first layer (42) to form an inflation chamber (28). A third layer (36) of flexible material (12) is coupled to the first and second layers so that a space is formed between the second and third layers. The space formed between the second and third layers is in fluid communication with the inflation chamber (28) at an outlet (18). The space between the second and third layers is formed so that a fluid channel (30) extends from a first end of the space between the second and third layers to the outlet (18). A plurality of spacer members (34) maintains the separation between the second and third layers so that the fluid channel (30) remains unobstructed even when the apparatus is folded or wrapped around an injured area.

Ireland Patent Number IE950163

Inventor

Paul Theodore Kolan, et al.

Issued

Dec. 12, 1995

An apparatus for applying closed-loop temperature controlled cold and heat therapy, with or without tactile stimulation, to an injured or otherwise traumatized part of the human or mammalian body. The apparatus comprises an easily transportable unit containing the insulated water reservoir, an integrated pump/heat exchanger powered by a small electric motor, microprocessor-based electronic temperature and fluid controls, and a pair of insulated fluid supply lines connected to a sealed bladder which is applied on or at the therapy site and held in place by means of a strap or wrap device. The cold/heat therapy is applied by re-circulating water from the heat exchanger through the bladder and back to the heat exchanger at a fixed rate which maintains the bladder at a constant temperature regardless of the heat load presented by the therapy site. The desired therapy temperature may be preset by the user or programmed to follow a desired therapy temperature profile. Therapy temperature is monitored by internal thermistors located in each of the fluid supply lines. The microprocessor-based control electronics monitor the thermistor output and control the pump/heat exchanger to maintain the preset therapy temperature or follow the pre-programmed therapy temperature profile. Tactile stimulation of the therapy site is created while maintaining the desired temperature at the therapy site by controlling the pump pressure such that the fluid pressure imposed upon the bladder varies in a cyclical manner, causing the bladder to expand and contract thereby creating tacticle stimulation, while maintaining the desired temperature at the therapy site via the heat exchanger. The tactile stimulation greatly increases the comfort of the cold therapy, thereby promoting longer and more beneficial therapy sessions. When used for cold therapy, the water or other fluid in the reservoir, which is mixed with the re-circulation water via the heat exchanger under control of the microprocessor, may be cooled using a multitude of mediums, such as block ice, ice cubes, crushed ice, sealed re-usable cold sources, or other readily available cold source. Similarly, when used for heat therapy, the reservoir fluid may be pre-heated externally before being placed in the reservoir or be actively heated via an immersible heater separate from the main unit. The therapy unit may be connected to a multitude of bladder shapes and designs for various therapy applications, or multiple bladders fluidly connected in series. The bladders are designed to accommodate substantial expansion and contraction in response to the varying pressures imposed by the pump to enhance the magnitude of tactile stimulation.

International Patent Application Number WO 2005/007060

Inventor

Overton Parish

Issued

Jan. 27, 2005

A sequential compression and temperature therapy blanket with a plurality of air chambers is disclosed. The air chambers are filled and released by a value assembly that may be separate from or integrated within the blanket. The temperature therapy blanket includes a fluid bladder for delivering hot and/or cold therapy to a patient. The temperature therapy blanket may also include an air bladder for providing compression.

While these compression wraps may be suitable for the purposes for which they were designed, they would not be as suitable for the purposes of the present invention, as hereinafter described.

SUMMARY OF THE PRESENT INVENTION

A primary object of the present invention is to provide a compression wrap having means for selectively applying pressure to a portion of said wrap.

Another object of the present invention is to provide a compression wrap having a top layer and a bottom layer with a bladder therebetween of smaller dimension than the wrap.

Yet another object of the present invention is to provide a compression wrap having an exterior valve in communication with said bladder.

Still yet another object of the present invention is to provide a separate hand-bulb that is matingly engagable to said valve.

Another object of the present invention is to provide a compression valve having a release valve in communication with said bladder.

Additional objects of the present invention will appear as the description proceeds.

The present invention overcomes the shortcomings of the prior art by providing a compression wrap for application to body members having a top layer and a bottom layer with an inflatable bladder of smaller dimension positioned therebetween, an interiorly positioned pocket for insertion of a gel pack and a hand-bulb for increasing the pressure within the bladder and thereby applying pressure to the gel pack. A release valve is incorporated into the bulb for selectively releasing the bladder pressure.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
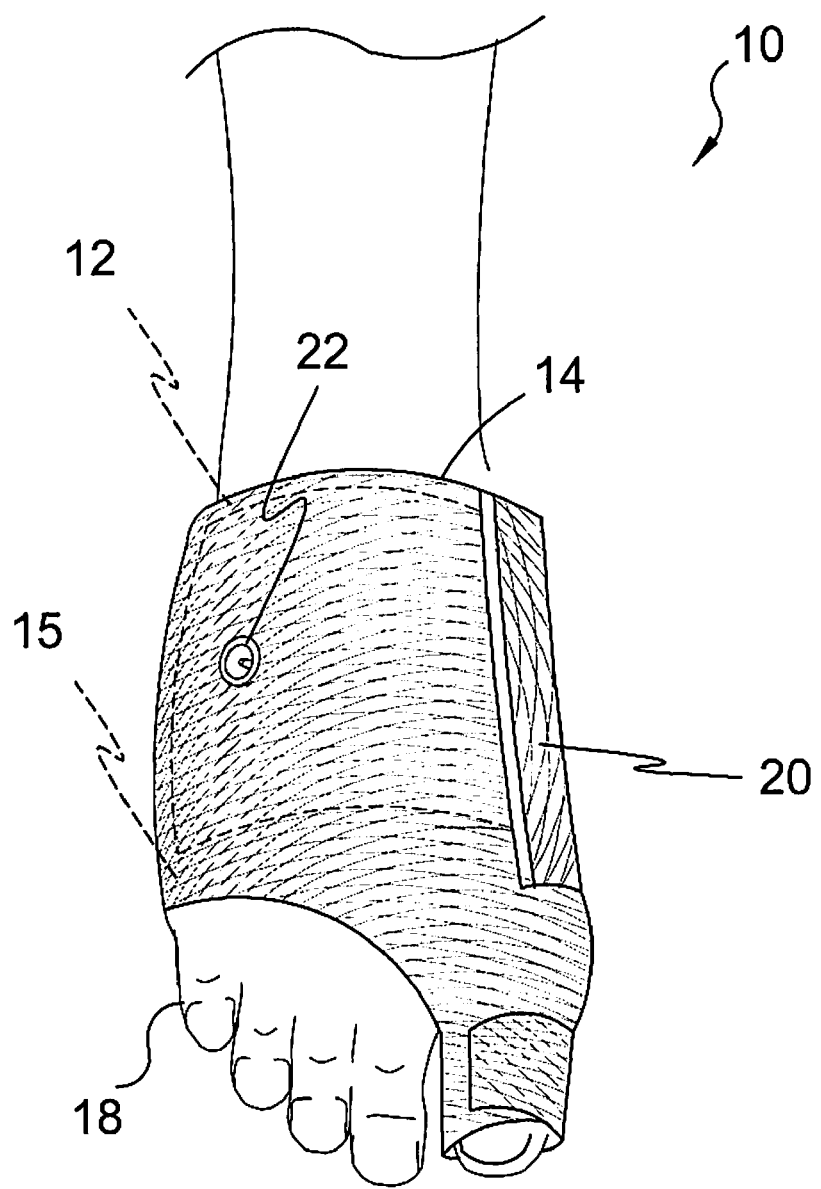
FIG. 1 is an illustrative view of the present invention in use.

Turning now descriptively to the drawings, in which similar reference characters denote similar elements throughout the several views, the figures illustrate the Inflatable Orthopedic Compression Wrap of the present invention. With regard to the reference numerals used, the following numbering is used throughout the various drawing figures.

- 10 Inflatable Orthopedic Compression Wrap of the present invention
- 12 inflatable bladder
- 14 top layer of 10
- 15 bottom layer of 10
- 18 foot
- 20 hook and loop fastener elements
- 22 air intake/release valve
- 24 pocket
- 26 hand bulb
- 28 one way valve
- 30 hand
- 32 air intake
- 34 air release
- 36 gel pack(s)
- 38 impinged pressure

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention 10 in use. The present invention is an inflatable compression wrap 10 for application to body members having a top layer 14 and a bottom layer 15 with an inflatable bladder 12 of smaller dimension positioned therebetween. On the interior side of the compression wrap is a pocket for insertion of a hot or cold substance. Shown is the compression wrap 10 disposed on a foot or appendage 18 and secured thereto with hook and loop fastener elements 20. An air intake and release valve 22 is provided to inflate and deflate the bladder 12 accordingly.

Figure 2:
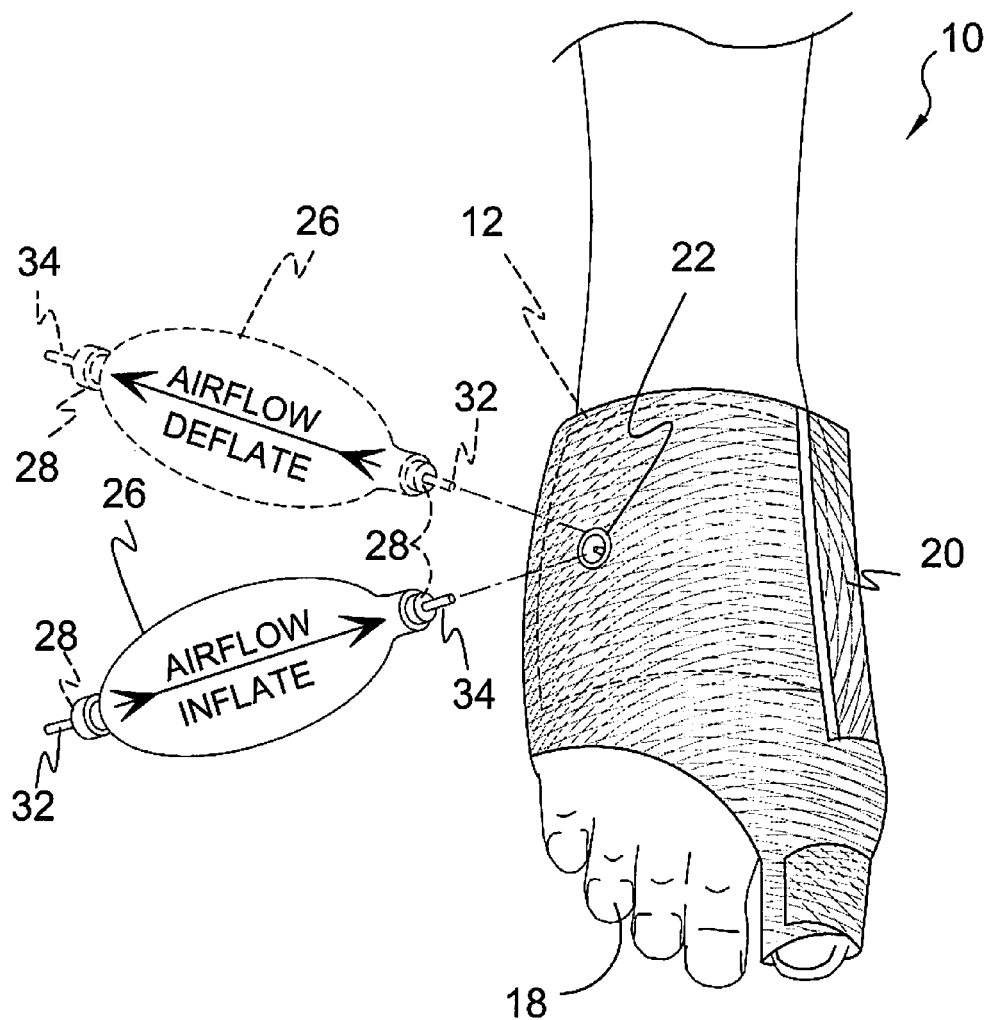
FIG. 2 is an illustrative view of the present invention in use.

FIG. 2 is an illustrative view of the present invention 10 in use. As aforementioned, the orthopedic compression wrap of the present invention 10 provides a pocket for inserting a gel pack and an inflatable bladder 12 for apply pressure to the gel pack. Once the wrap is secured around the appendage 18 with hook and loop fastener elements 20 the user takes the provided hand-bulb 26 having one-way valves 28 on each end and attaches the air release valve 34 which will inflate the bladder to the wrap's valve 22 and proceeds to inflate 26 by depressing the bulb 26. To deflate the wrap the bulb 26 is reversed so the air intake valve 32 is connected to the wrap valve 22 with the air release valve 34 exhausting to the environment as the bulb is depressed.

Figure 3:
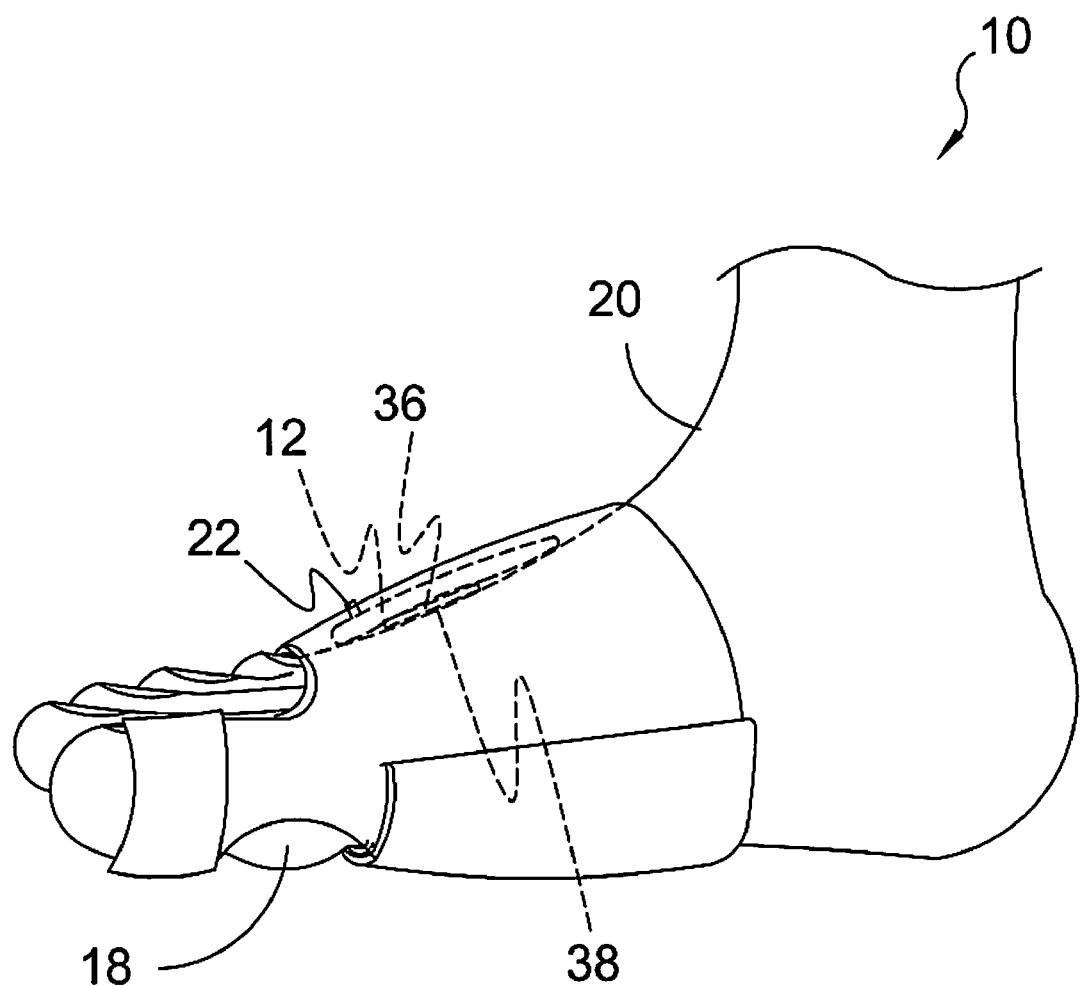
FIG. 3 is an illustrative view of the present invention in use.

FIG. 3 is an illustrative view of the present invention 10 in use. For clarity of illustration the gel pack 36, bladder 12 and valve 22 are shown working in concert to impinge pressure 38 upon the foot. The actual location of the bladder, valve, pocket and gel pack is a design consideration dependant upon the type of pressure wrap required. The compression wrap of the present invention 10 provides means for a user to selectively apply applying pressure to a gel pack selectively positioned within the pocket of the compression wrap and means for relieving the pressure when desired. The compression wrap 10 is secured to the foot 18 with hook and loop fastener elements 20.

Figure 4:
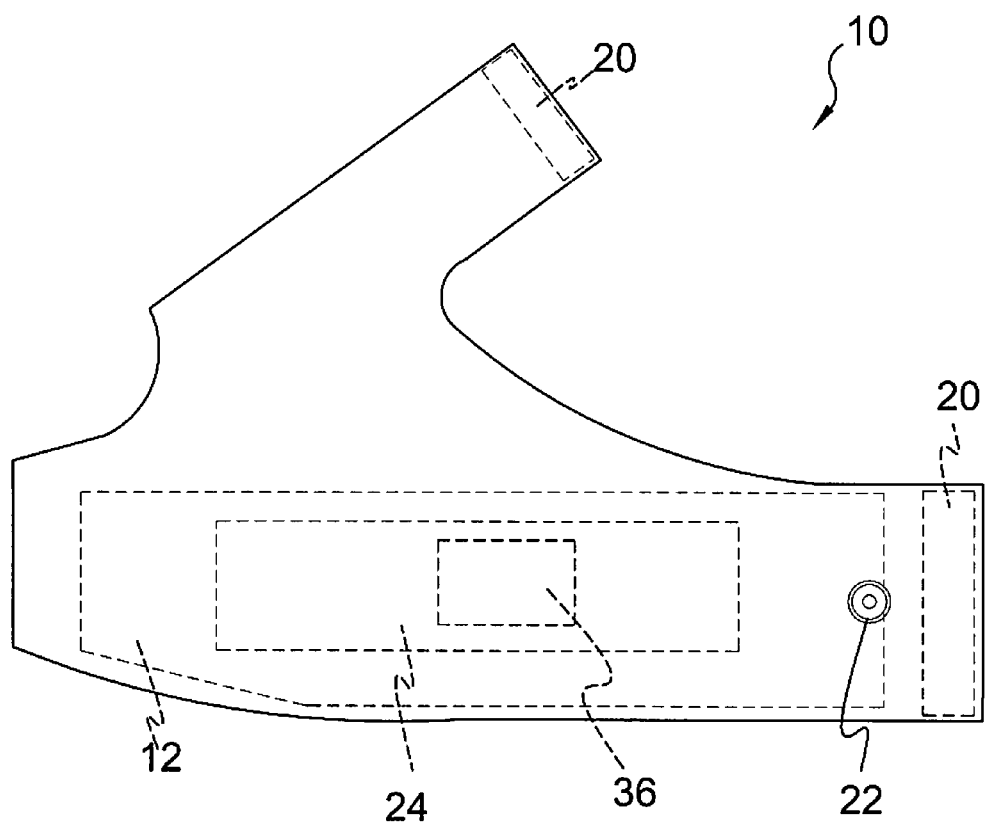
FIG. 4 is an exterior view of the compression wrap of the present invention.

FIG. 4 is an exterior view of the compression wrap of the present invention 10. The present invention is a compression wrap 10 for application to a user comprising a flexible band having attachment portions whereby the wrap can be selectively coupled, an interiorly positioned pocket 24 for placement of an inflatable bladder 12 and a hot or cold gel pack 36, a valved compartment immutably formed within the flexible band and a hand-bulb for inflating the valved compartment through the air intake/release valve 22 by applying pressure to the gel pack 36 within said pocket 24.

Figure 5:
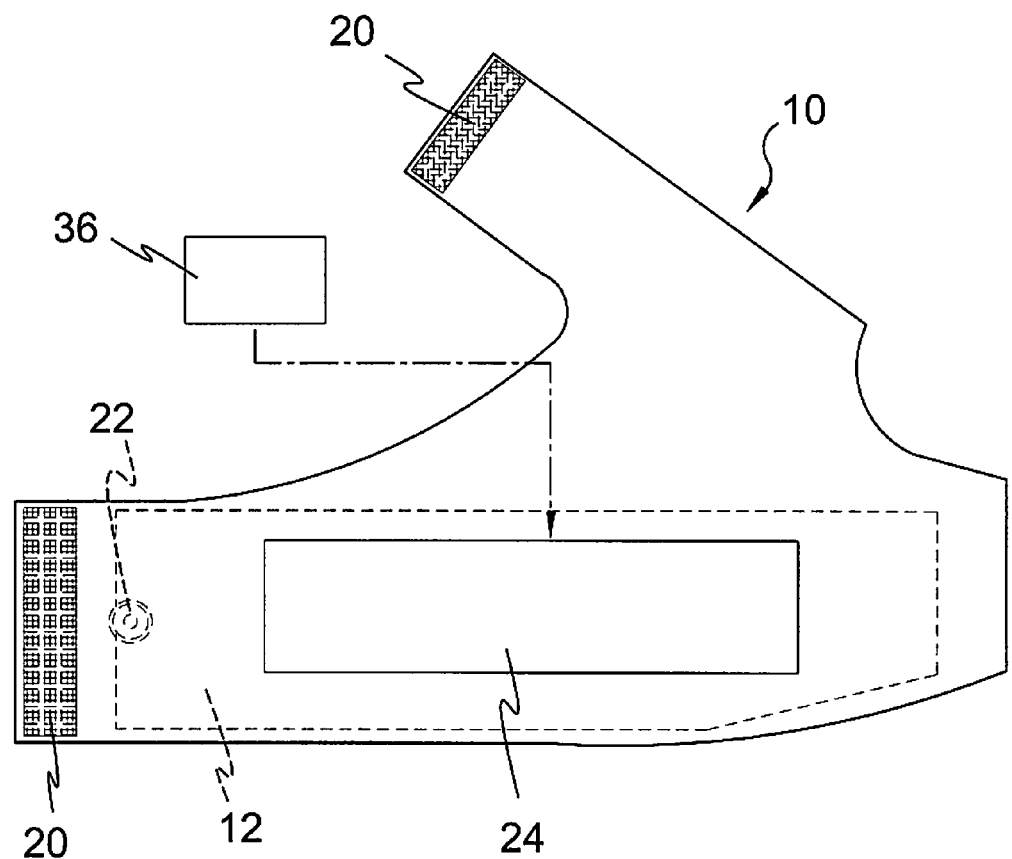
FIG. 5 is an interior view of the compression wrap of the present invention.

FIG. 5 is an interior view of the compression wrap of the present invention 10. Shown is the interior side of the present invention having an insert pocket 24 for the selective placement of a reusable gel pack 36. Hook and loop fastener elements 20 are provided for closure to the pliable wrap. An intake/release valve 22 is located within the wrap is inflated by means of a hand bulb, providing means for applying pressure to create compression within the bladder 12 upon the gel pack 36.

Figure 6:
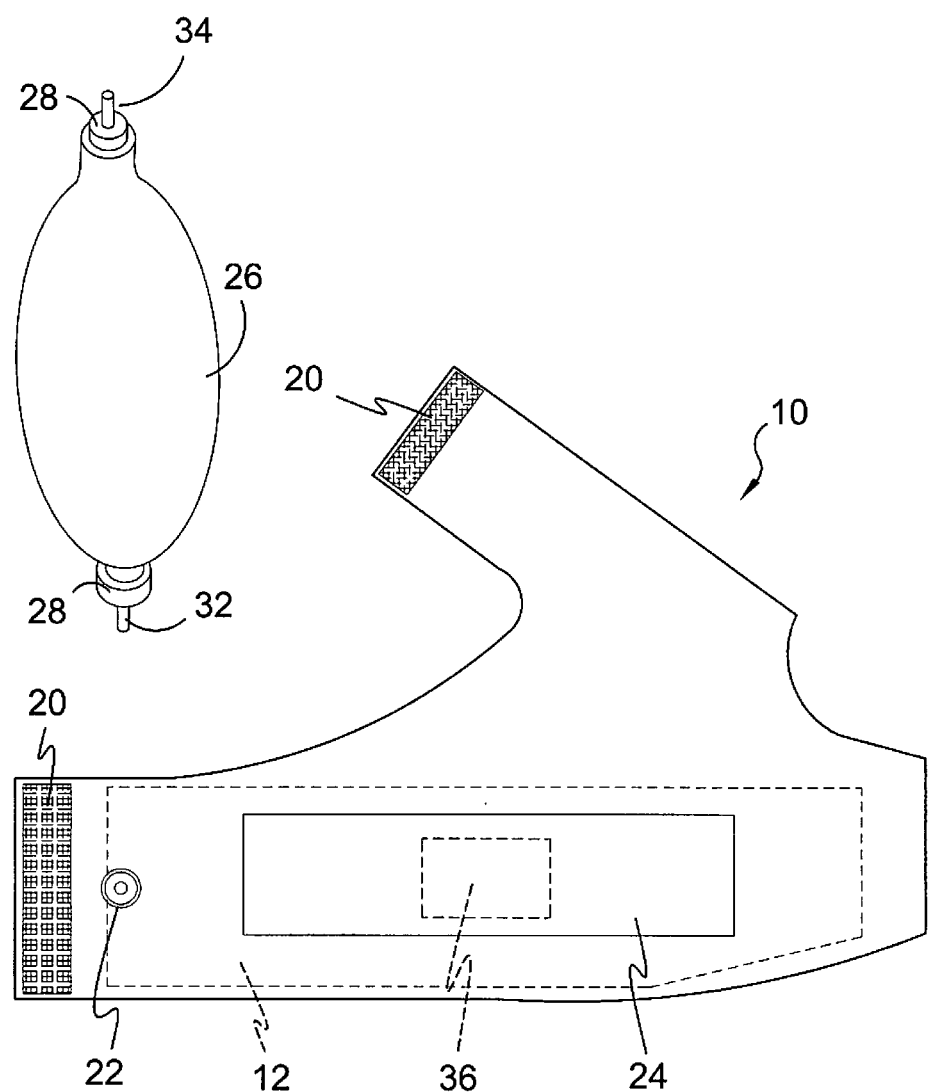
FIG. 6 is an interior view of the compression wrap having a gel pack within the pocket.

FIG. 6 is an interior view of the compression wrap of the present invention 10. Shown is the interior side of the present invention having an insert pocket 24 for the selective placement of a reusable gel pack 36. Hook and loop fastener elements 20 are provided for closure to the pliable wrap. An intake/release valve 22 is located within the wrap is inflated by means of a hand bulb, providing means for applying pressure to create compression within the bladder 12 upon the gel pack 36.

Figure 7:
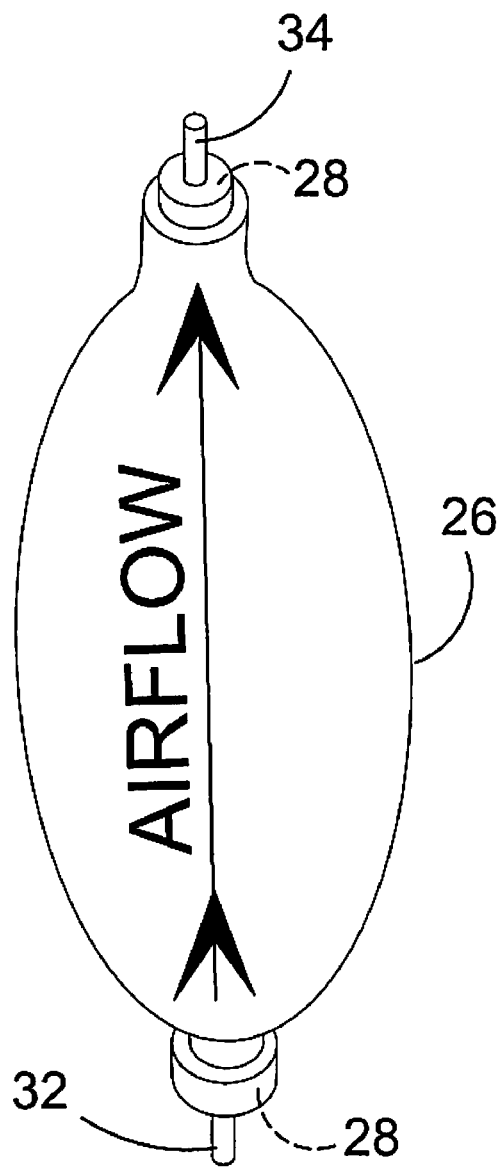
FIG. 7 is an illustrative view of the hand pump bulb.

FIG. 7 is an illustrative view of the hand pump bulb 26. The present invention includes a pressure release mechanism 26 for reducing pressure within the bladder. When the bulb 26 is inserted into the air intake/release valve dependant on which end is inserted into the bladder, the air is either driven into the bladder via air exhaust valve 34 or air is withdrawn from the bladder by attaching air intake valve 32 to the bladder. Each end of the bulb contains a one-way valve 28.

Figure 8:
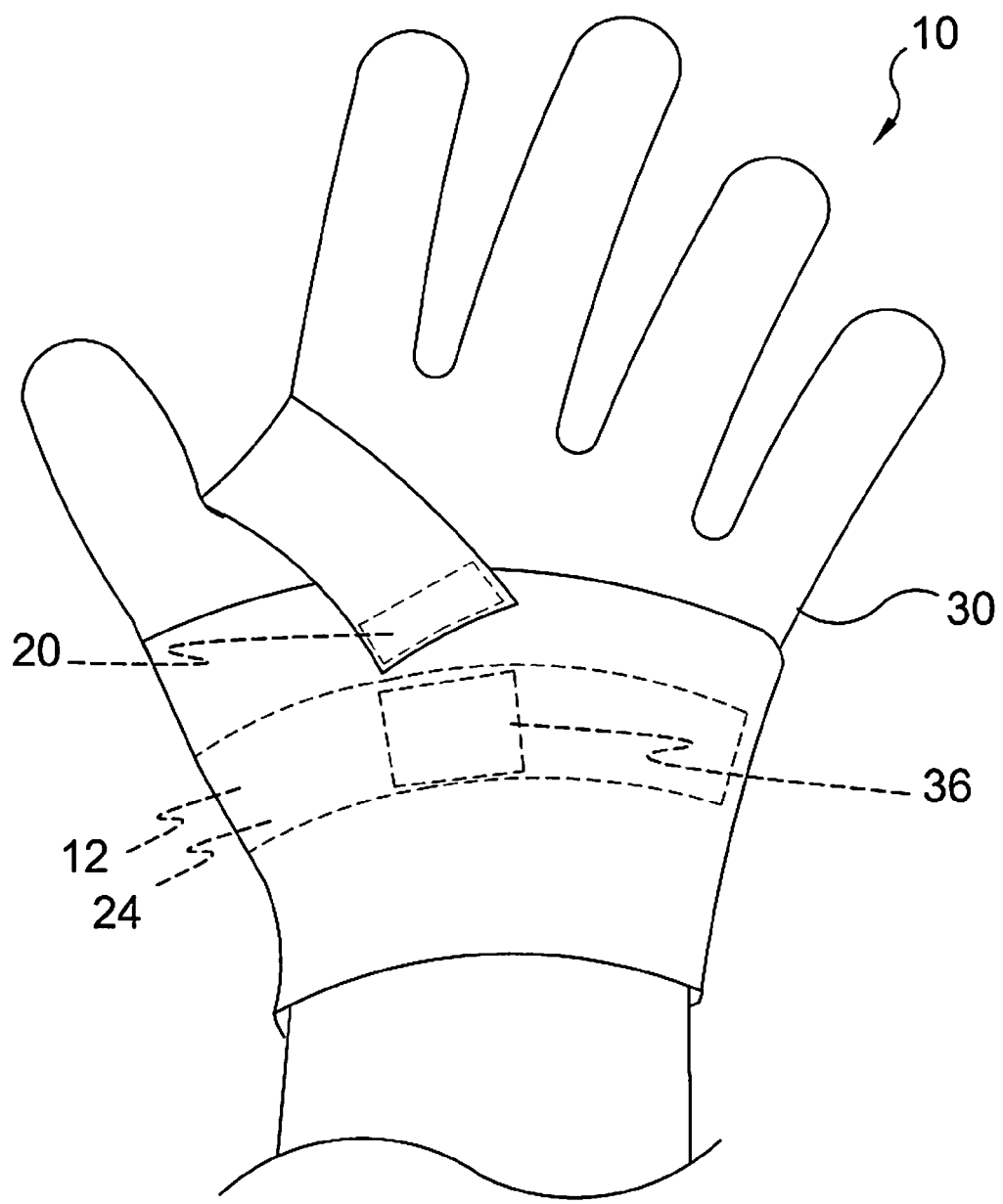
FIG. 8 is an illustrative view of the pressurable compression wrap used on a hand.

FIG. 8 is an illustrative view of the pressurable compression wrap used on a hand. Shown is the present invention 10, a compression wrap applied to a user's hand 30 comprising a flexible band having attachment portions whereby the wrap can be selectively coupled with hook and loop fastener elements 20. An air bladder 12 with a pocket 24 is provided so that the pliable receptacle having a hot or cold substance gel pack 36 placed therein can be applied to a desired area. Said flexible band provides a valved compartment immutably formed within the flexible band that is inflated by a hand bulb providing means for applying pressure to the pliable receptacle when in use.

Figure 9:
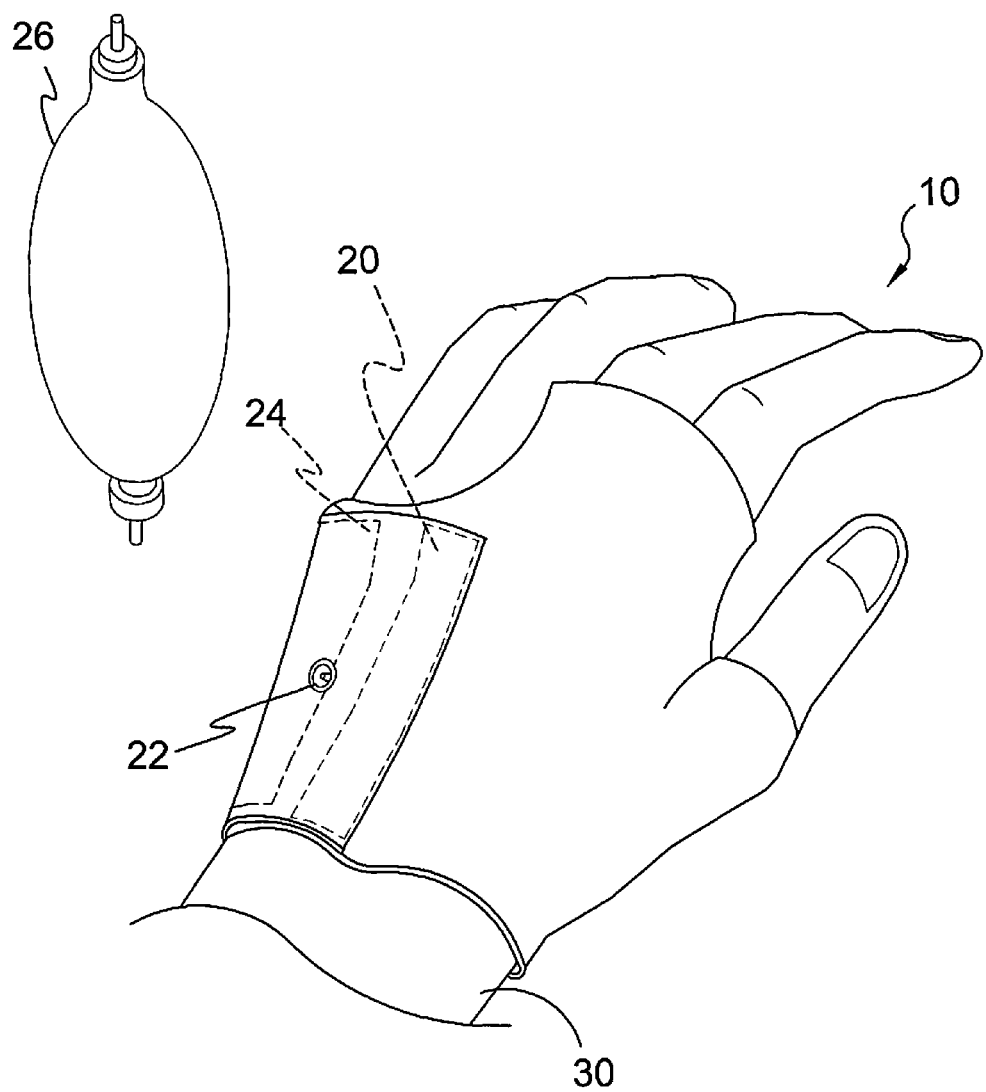
FIG. 9 is an illustrative view of the pressurable compression wrap in use on a hand.

FIG. 9 is an illustrative view of the pressurable compression wrap in use on a hand. Shown is the compression wrap of the present invention 10 applied to a hand 30 of a user and secured by hook and loop fastener elements 20. Also shown is a hand bulb 26 for inflating air through the air intake/release valve 22 for applying pressure to the bladder 12 when in use.

Figure 10:
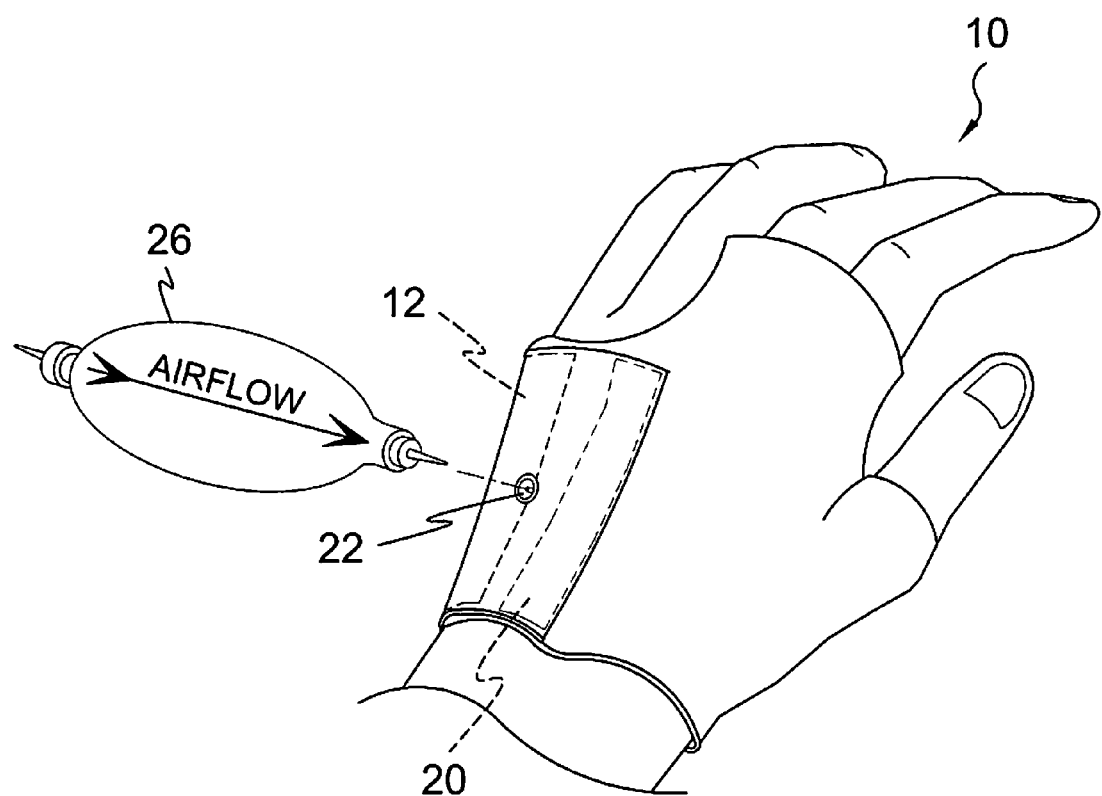
FIG. 10 is an illustrative view of the back hand portion of the present invention.

FIG. 10 is an illustrative view of the back hand portion of the present invention 10. Shown is the compression wrap of the present invention 10 for application to the hand 30 wherein a hand held bulb 26 is used to increase the pressure within the bladder 12 by introducing air therein through the air intake/release valve 22.

Figure 11:
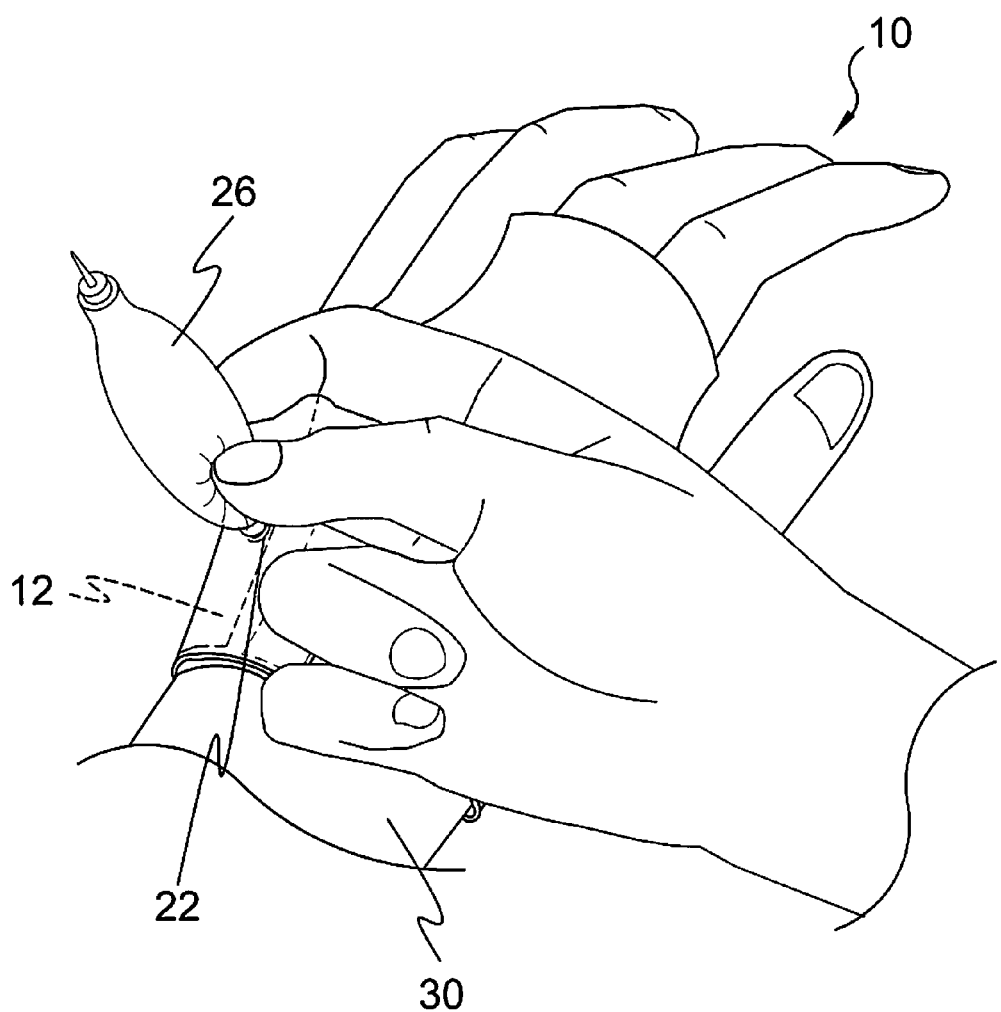
FIG. 11 is an illustrative view of the present invention in use.

FIG. 11 is an illustrative view of the present invention 10 in use. The present invention 10 is a compression wrap comprising a flexible band having attachment portions whereby the wrap can be selectively coupled. A pocket is provided on the inner hand portion so that a reusable hot or cold gel pack can be placed therein and be applied to a desired area using said flexible band. The flexible band provides an inflatable bladder 12 formed within the flexible band and is inflated by a hand 30 held "hand bulb" 26 inserted into the air intake/release valve 22 providing means for applying pressure to the pliable receptacle when in use.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An orthopedic compression wrap for use on a foot comprising:
    a) a wrap member having a top side and a bottom side; a main portion adapted to be wrapped around a sole of said foot, and an extended portion adapted to be wrapped around one toe of said foot;
    b) an inflatable bladder disposed within a pocket in said main portion of said wrap member, said bladder having an intake/release valve extending through said top side of said wrap member, said pocket also containing a cold or heated gel pack;
    c) means for inflating or deflating said bladder comprising a hand pump bulb having an intake valve at one end and a release valve on an opposite end, each valve of said hand pump bulb engageable with said intake/release valve whereby said bladder can be filled or exhausted using said hand pump bulb depending upon which valve in said hand pump bulb is connected to said intake/release valve of said bladder, said valves in said hand pump bulb are coupled to nozzles that are mateable to the wrap's air intake/release valve;
    d) means adapted to secure said wrap member to said foot to be treated; and
    e) wherein when said wrap is placed on the foot of a user the extended portion encircles only a single toe and the pocket is positioned on an upper surface of the users foot.

2. The orthopedic compression wrap recited in claim 1, wherein said securing means is separate hook and loop fastener elements for said main position and said extended portion.

3. A method of applying pressure to a thermal agent during hot or cold compress therapy to the foot of a user, the method comprising:
    a) providing a carrier for the thermal agent in a pocket of said carrier, said carrier being releasably fastenable to the target area;
    b) attaching the carrier to the the foot of the user so that said pocket of said carrier is positioned on an upper surface of the users foot when the carrier is wrapped around the users foot and an extended portion of the carrier is wrapped around a single toe;
    b) providing the carrier with a bladder inside of said pocket, said bladder having a valve for increasing and decreasing bladder pressure;
    c) providing a hand held pump having a pair of nozzles that are matingly engageable to the bladder valve, each nozzle having a one-way valve and one of said pair of nozzles for inflating and the other of said pair of nozzles for deflating; and
    d) attaching the hand held pump to the bladder valve and pumping until a desired pressure within the bladder is achieved thereby applying a consistent pressure to the thermal agent during thermal therapy.

4. The method of claim 3, further comprising means for deflating said bladder comprising mounting the hand pump in a reverse direction and pumping to remove the air from said bladder.

* * * * *